United States Patent
Maciejewski et al.

(10) Patent No.: US 11,602,492 B2
(45) Date of Patent: Mar. 14, 2023

(54) NON-RINSE MICELLAR WATER CHASSIS

(71) Applicant: Johnson & Johnson Consumer Inc., Skillman, NJ (US)

(72) Inventors: Jessica Maciejewski, Springfield, PA (US); Alexandria Dinapoli Marzano, Plainsboro, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 16/814,392

(22) Filed: Mar. 10, 2020

(65) Prior Publication Data

US 2020/0306149 A1 Oct. 1, 2020

Related U.S. Application Data

(60) Provisional application No. 62/823,043, filed on Mar. 25, 2019.

(51) Int. Cl.
| | | |
|---|---|---|
| *A61K 8/02* | (2006.01) | |
| *A61K 8/34* | (2006.01) | |
| *A61K 8/41* | (2006.01) | |
| *A61Q 19/10* | (2006.01) | |

(52) U.S. Cl.
CPC ............ *A61K 8/0291* (2013.01); *A61K 8/345* (2013.01); *A61K 8/416* (2013.01); *A61Q 19/10* (2013.01); *A61K 2800/10* (2013.01); *A61K 2800/262* (2013.01); *A61K 2800/524* (2013.01); *A61K 2800/5422* (2013.01); *A61K 2800/596* (2013.01)

(58) Field of Classification Search
CPC ...... A61K 8/0291; A61K 8/345; A61K 8/416; A61K 2800/10; A61K 2800/262; A61K 2800/524; A61K 2800/5422; A61K 2800/596; A61Q 19/10
See application file for complete search history.

(56) References Cited

U.S. PATENT DOCUMENTS

| | | | |
|---|---|---|---|
| 7,446,088 B2 * | 11/2008 | Fevola | A61K 8/604 |
| | | | 510/475 |
| 8,961,945 B2 * | 2/2015 | Fevola | C07D 319/12 |
| | | | 424/70.1 |
| 2008/0268188 A1 | 10/2008 | Cunningham et al. | |
| 2011/0142965 A1 | 6/2011 | Walke | |
| 2016/0303043 A1 | 10/2016 | Khoury | |

FOREIGN PATENT DOCUMENTS

| | | |
|---|---|---|
| EP | 2468842 A1 | 6/2012 |
| EP | 2816101 A1 | 12/2014 |

OTHER PUBLICATIONS

International Search Report; PCT/IB2020/052113; dated May 27, 2020.

\* cited by examiner

*Primary Examiner* — Snigdha Maewall
(74) *Attorney, Agent, or Firm* — Laura A. Donnelly

(57) ABSTRACT

A non-rinse micellar water composition; method of manufacture for a non-rinse micellar water composition; and a method of use for a micellar water composition are disclosed.

3 Claims, 5 Drawing Sheets

Micelle formation around oil

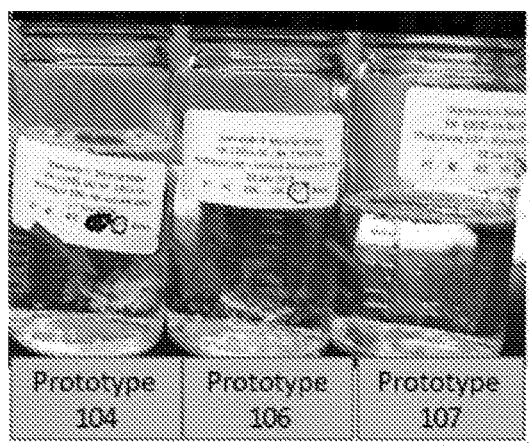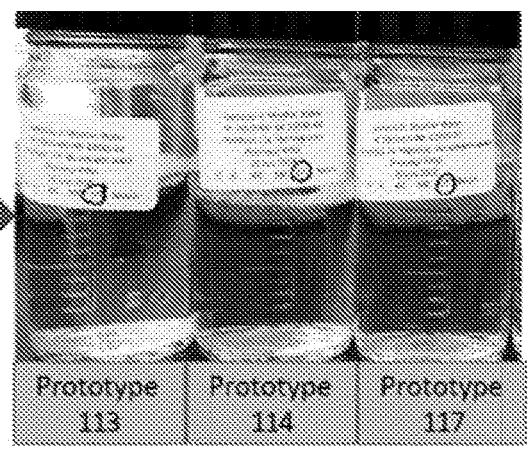
Samples containing
Sodium Benzoate
Samples containing
Phenoxyethanol and Ethylhexylglycerin
*FIG. 4*
*FIG. 5*

Precipitate in a micellar water
sample formed over 4 weeks

NON-RINSE MICELLAR WATER CHASSIS

FIELD OF THE INVENTION

The present invention relates to a personal care product and, in particular, to a gentle cleansing non-rinse micellar water composition that provides a quick, gentle cleanse from head-to-toe between bath time or on-the-go.

BACKGROUND OF THE INVENTION

Surfactants are compounds that lower the surface tension (or interfacial tension) between two liquids, between a gas and a liquid, or between a liquid and a solid. Surfactants, which may act as detergents, wetting agents, emulsifiers, foaming agents, and dispersants, are made of a hydrophilic head and a hydrophobic carbon-carbon chain tail. Most commonly, surfactants are classified according to polar head group. A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed amphoteric.

Surfactants are not without disadvantages. For example, some surfactants, such as sulfates, including alkyl sulfates and alkyl ether sulfates, are known to be irritating to the skin. Prolonged exposure to surfactants can irritate and damage the skin because surfactants disrupt the lipid membrane that protects skin and other cells. Skin irritancy generally increases in the series nonionic, amphoteric, anionic and cationic surfactants.

The biodegradability of a surfactant is determined by its hydrophobic hydrocarbon group.

When surfactants are added to water, they aggregate themselves with the hydrophilic head groups facing outward and the hydrophobic tails orient inwards to form micelles. See FIG. 1. Micellar waters are non-viscous surfactant systems that contain micelles to provide cleansing efficacy.

When the micelles are wiped or rinsed from the skin, dirt and oil are removed as well.

SUMMARY OF THE INVENTION

The invention relates to a mild non-rinse micellar water composition with superior cleansing efficacy. The inventive non-rinse micellar water composition comprises amphoteric and non-ionic surfactants. Further, the non-rinse micellar water composition is free of glycol and exhibits a total transparency and a superior mildness.

DESCRIPTION OF THE FIGURES

FIG. 4 shows samples containing sodium benzoate.
FIG. 5 shows samples containing phenoxyethanol and ethylhexylglycerin.

DETAILED DESCRIPTION OF THE INVENTION

Definitions

The non-rinse micellar water composition of the invention serves to replace water and preferably is a transparent liquid that appears clear, colorless, and transparent like water to simulate the physical appearance of water.

Humectants, such as natural glycerin, may be included in the non-rinse micellar water composition to maintain the constitution, e.g., the moisture content, of the composition and to promote a fresh feeling for the skin after the composition is allowed to evaporate from the skin or is wipe off from the skin.

Preservatives, such as phenoxyethanol, may be included in the non-rinse micellar water composition.

Chelating agents, such as tetrasodium glutamate diacetate, may be included in the non-rinse micellar water composition to temporarily reduce the surface tension of water, creating a sheeting effect and helping make suds and grime rinse away quickly and completely.

A pH adjuster, such as citric acid and sodium citrate, may be included in the non-rinse micellar water composition to either raise or lower the pH as needed so that the non-rinse micellar water is less irritating to the skin.

Fragrances may also be included in the non-rinse micellar water composition. A very light scent that conveys freshness is preferred, such as a scent that mimics the scent of soap or baby powder; a citrus, such as lemon or lime; or a botanical-based essential oil, such as lavender, rose petals, calendula, peppermint, mint, nettle, spearmint, menthol, or any botanical essential oil that can be produced from any part of a plant including the blossom, seeds, woods, and leaves.

The non-rinse micellar water composition of the invention preferably includes ingredients that are readily available.

Figure 1:
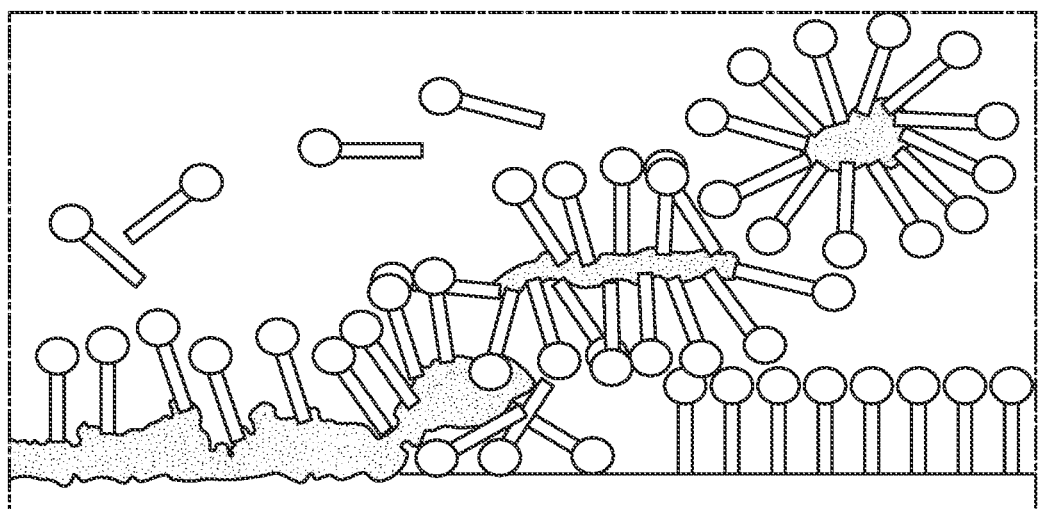
FIG. 1 is a schematic showing micelle formation.
Figure 2:
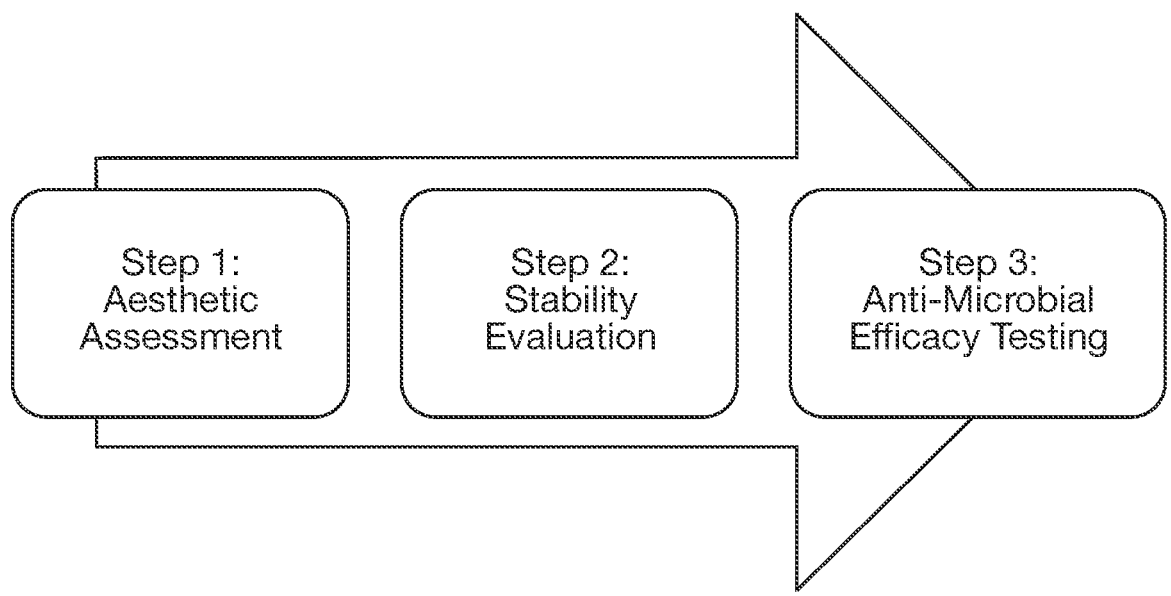
FIG. 2 is a schematic showing key attributes.
Figure 3:
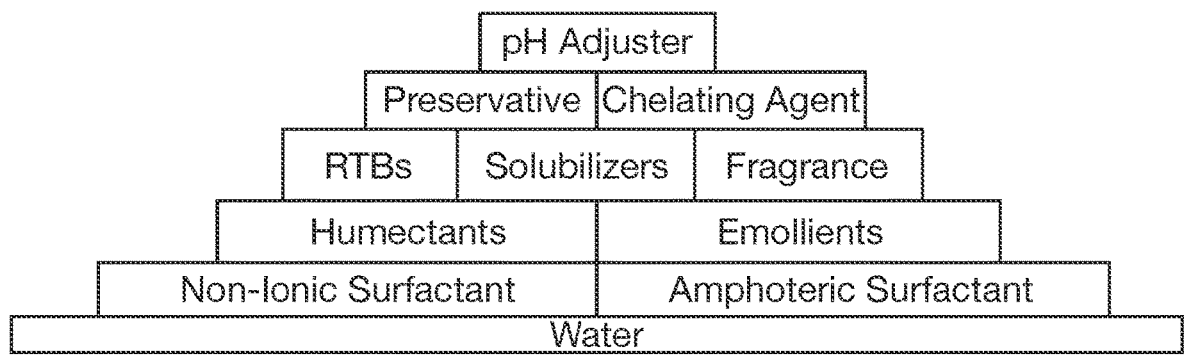
FIG. 3 is a schematic showing formulation strategy.
Figure 6:
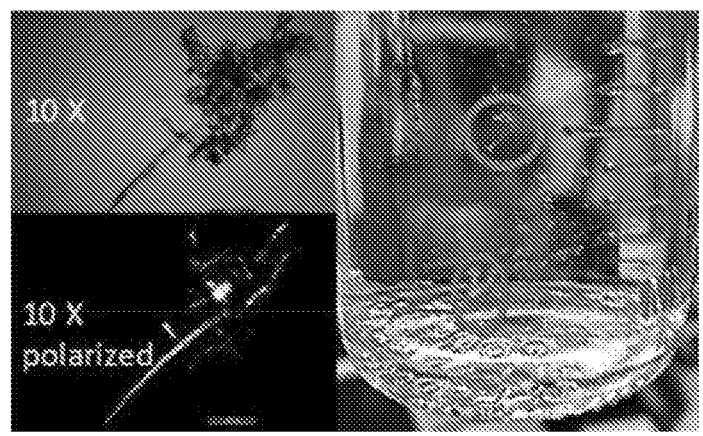
FIG. 6 shows precipitate in a micellar water.

Although the non-rinse micellar water composition is gentle, it is able to provide a robust cleansing system. In accordance with the invention, three key attributes, i.e., aesthetics, stability, and anti-microbial efficacy, were found to be dependent upon one another. See FIG. 2. Therefore, the pyramid structure in FIG. 3 outlines formulation strategy by starting at the bottom with the base ingredients that establish optimal aesthetics, and progressing upward to ingredients that stabilize the formula and provide anti-microbial efficacy.

Examples

Micellar water compositions were prepared as follows using the components in Table 1, wherein percentages are given by weight.

1. Heat purified water in main vessel to 70° C.
2. Add glycerin, sodium benzoate, sodium citrate, polysorbate 20, tetrasodium glutamate diacetate, glycereth-26, polyglyceryl-4 caprate (each, if present one at a time) and mix until uniform.
3. Once 50° C., add sucrose cocoate and heat to 70° C.
4. Once 70° C. is reached, keep heating for 10 minutes.
5. Turn off heat and begin cooling to 25-30° C.
6. Add cocamidopropyl betaine and glycereth-26 or cocamidopropyl hydroxysultaine (each if present) and mix until uniform.
7. Premix phenoxyethanol, ethylhexylglycerin, fragrance and glycerin (volcanic water) (each, if present) and hold.
8. Add premix to batch once it is below 40° C. and mix until uniform.
9. Adjust the pH with citric acid (solution 50%) if necessary.

TABLE 1

| Ingredient | Function | 104 | 106 | 107 | 113 | 117 | 148 |
|---|---|---|---|---|---|---|---|
| Water | Solvent | 94.71 | 95.16 | 95.31 | 94.76 | 94.26 | 94.01 |
| Sodium benzoate | preservative | 0.35 | 0.4 | 0.35 | N/A | N/A | 0.35 |
| Citric acid | pH adjuster | 0.24 | 0.24 | 0.24 | 0.24 | 0.24 | 0.24 |
| Glycerine (volcanic water) | Humectant | 0.5 | N/A | N/A | N/A | 0.5 | 0.5 |
| Sucrose cocoate | Non-ionic surfactant | N/A | 0.3 | 0.3 | 0.3 | 0.3 | N/A |
| Cocamidopropyl hydroxy sultaine (Mirataine CBS) | Amphoteric surfactant | N/A | N/A | 0.2 | 0.3 | 0.2 | 0.3 |
| Glycereth-26 | Humectant | 1.0 | 1.0 | 1.0 | 1.0 | 1.0 | 1.0 |
| Glycerin (same as glycerine) | Humectant | 0.5 | 0.5 | 0.5 | 0.5 | 0.5 | 0.5 |
| Cocamidopropyl betaine | Amphoteric surfactant | 0.3 | 0.3 | N/A | N/A | N/A | N/A |
| Polysorbate 20 | Non-ionic surfactant; Solubilizer | 2.0 | 2.0 | 2.0 | 2.0 | 2.0 | 2.0 |
| Sodium citrate | pH adjuster | N/A | N/A | N/A | 0.1 | 0.1 | N/A |
| Fragrance | Scent | 0.1 | 0.1 | 0.1 | 0.1 | 0.1 | 0.1 |
| Phenoxyethanol | Preservative | N/A | N/A | N/A | 0.3 | 0.3 | N/A |
| Ethylhexylglycerin | Humectant; solubilizer | N/A | N/A | N/A | 0.5 | 0.5 | 0.5 |
| Tetrasodium glutamate diacitate | Chelating agent | N/A | N/A | N/A | N/A | N/A | 0.2 |
| Polyglyceryl-4-caprate | Non-ionic surfactant | N/A | N/A | N/A | N/A | N/A | 0.3 |
| TOTAL | | 100 | 100 | 100 | 100 | 100 | 100 |
| Ph | | 5.0 | 4.48 | 4.44 | 5.77 | 5.36 | 5.00 |
| Stability | | 16 weeks | 16 weeks | 16 weeks | 16 weeks | 16 weeks | 16 weeks |

The following are some of the desired attributes that were considered when formulating:

Visual: Clear
After Feel: Soft, no residue
First Contact: Water consistency; non-sticky
Fragrance: Light, fresh, clean
Results are shown in Table 2 below.

TABLE 2

| Attributes | 104 | 117 | 148 |
|---|---|---|---|
| Clear | Yes | Yes | Yes |
| No precipitate formation | No (precipitate formed) | No (precipitate formed) | Neutral |
| Preferred aesthetics | Neutral | Yes | Yes |
| Passes freeze/thaw stability | No | Yes | Yes |
| Passes antimicrobial efficacy testing | Yes | No | Yes |

Observations Include:

Samples with non-ionic surfactant Tween alone had the worse clouding and precipitation.

Addition of ethylhexylglycerin stabilizes the formula.

Increase in polysorbate 20 increased precipitate.

Addition of PEG-40 hydrogenated castor oil accelerated precipitate formation

Addition of volcanic water decrease in precipitation

Example

Modifications were made to a lead prototype, Prototype 148, to assess the ten sensory attributes set forth in Table 3 below. Prototype 148 was altered as follows:

Prototype A: Replaced sodium benzoate with phenoxyethanol
Prototype B: Replaced glycereth-26 with glycerin at 1:1 ratio
Prototype C: Replaced polyglyceryl-4 caprate with sucrose cocoate at 1:1 ratio
Prototype D: Removed glycereth-26

TABLE 3

| Compared to 148 | | A | B | C | D |
|---|---|---|---|---|---|
| Scent | Strength | = | = | = | = |
| Application | Wetness on fingers | NEU | = | = | = |
| | Drag | = | NEG | = | POS |
| | # of rotations | = | = | = | = |
| Feel on skin | Wetness on arm | NEU | = | = | = |
| | Cooling sensation | NEG | = | POS | NEG |
| | Drag | = | = | POS | = |
| | Stickiness | POS | = | = | = |
| | Smoothness | POS | = | = | = |
| Residue feel | Residue amount | POS | = | NEG | = |
| | Oiliness/greasiness | = | POS | = | POS |
| | Waxiness | POS | POS | NEG | = |

=—same
NEG—negative
NEU—neutral
POS—positive

Prototype A had the most significant number of positive attributes when compared to the other prototypes tested.

Proposed Packaging and Method of Use

The non-rinse micellar water composition can be provided to the consumer in a container, e.g., a bottle. Individual packettes enclosing measured portions of the non-rinse micellar water composition may also be used. To dispense the non-rinse micellar water composition from a bottle, a pump, squeezable valve, or a removable screw cap may be used. The non-rinse micellar water composition can be dispensed onto either one or both of (a) a palm of one's hand and (b) a cotton pad or a cloth such as a wash cloth as a means to transport the non-rinse micellar water composition to a desired area of the body. The cotton pad or cloth saturated with the non-rinse micellar water composition can be swept across the skin to remove dirt and oil.

The embodiments of the invention are believed to be safe to use and different from many rinseless body wash products currently available in the personal care market as they include only ingredients with no known negative health related consequences.

It will be understood that, while various aspects of the present disclosure have been illustrated and described by way of example, the invention claimed herein is not limited thereto, but may be otherwise variously embodied according to the scope of the claims presented in this and/or any derivative patent application.

The invention claimed is:

1. A non-rinse micellar water composition, comprising:
    greater than about 90% by weight water;
    from about 0.25% to about 5.0% surfactant selected from the group consisting of polysorbate 20 and polyglyceryl-4-caprate;
    from about 0.25% to about 5% humectant selected from the group consisting of glycerin; ethylhexylglycerin; and glycereth-26; and
    from about 0.25% to about 0.5% preservative, wherein the preservative is phenoxyethanol;
    wherein the non-rinse micellar water composition is free of glycol; and
    wherein the non-rinse micellar water composition simulates the physical appearance of water, and
    wherein the non-rinse micellar water composition is stable with antimicrobial efficacy.

2. The non-rinse micellar water composition according to claim 1, wherein the non-rinse micellar water composition has an appearance that is transparent.

3. A method of cleansing a body, comprising applying the non-rinse micellar water composition of claim 1 externally to the body.

* * * * *